(12) United States Patent
Rashman et al.

(10) Patent No.: US 6,308,798 B1
(45) Date of Patent: Oct. 30, 2001

(54) LIGHTWEIGHT STETHOSCOPE WITH VARIABLE DIAPHRAGM AND BELL COMPONENTS

(75) Inventors: Richard Rashman, Los Angeles; Dennis Shick, Burbank, both of CA (US)

(73) Assignee: Prestige Medical Corporation, Northridge, CA (US)

( * ) Notice: Subject to any disclaimer, the term of this patent is extended or adjusted under 35 U.S.C. 154(b) by 798 days.

(21) Appl. No.: 08/635,483

(22) Filed: Apr. 22, 1996

(51) Int. Cl.[7] ............................................. A61B 7/02
(52) U.S. Cl. ................................................. 181/131
(58) Field of Search ........................... 181/131, 132, 181/137; D24/134

(56) References Cited

U.S. PATENT DOCUMENTS

| | | | |
|---|---|---|---|
| 2,233,087 | * 2/1941 | Tynan | 181/131 |
| 2,513,827 | * 7/1950 | Tynan | 181/131 |
| 2,719,594 | * 10/1955 | Smithline | 181/137 |
| 2,722,989 | * 11/1955 | Tynan | 181/131 |
| 3,035,656 | * 5/1962 | Kebel | 181/137 |
| 3,275,099 | * 9/1966 | Speelman | 181/131 |
| 3,316,998 | * 5/1967 | Krug | 181/137 |
| 4,239,089 | * 12/1980 | Nelson | 181/131 |

\* cited by examiner

*Primary Examiner*—David M. Gray
(74) *Attorney, Agent, or Firm*—Blakely Sokoloff Taylor & Zafman

(57) ABSTRACT

A stethoscope including a dual head chest piece with removable diaphragm structures and bell components for adapting the stethoscope for use with infants or adults, or on sites having less skin area, such as the ribs. The stethoscope further includes a single tube for connecting the chest piece to the ear piece. Because the stethoscope uses only a single tube sound passage system, the stethoscope is smaller and lighter in weight, and thus, less cumbersome and less costly to make than the traditional convertible dual head stethoscope.

4 Claims, 5 Drawing Sheets

LIGHTWEIGHT STETHOSCOPE WITH VARIABLE DIAPHRAGM AND BELL COMPONENTS

BACKGROUND OF THE INVENTION

This invention relates generally to stethoscopes and, more particularly, to stethoscopes with detachable diaphragm and bell components which adapt the stethoscope for use on infants, or adults, and in locations of smaller skin areas.

The chest piece of most stethoscopes are the dual head type which consist of a diaphragm on one side and a bell on the other. The diaphragm is suitable for detecting low frequency range sounds associated with diastolic and third heart sounds; the bell is suitable for detecting higher frequency range sounds, such as those which signify murmurs. The chest piece also has a revolvable valve stem which the user rotates to open the desired sound passage. FIGS. 2 and 3 show a typical dual head stethoscope. Typically, for the best detection of sounds, it is desirable to acoustically seal the rim of the diaphragm or bell with the skin of the patient's body above the site to be auscultated. Thus, a diaphragm suitable for use with an adult, is too large to be used on an infant's chest, and conversely, a diaphragm suitable for use with an infant is too small to be used on an adult. As another example, the region between ribs, is more narrow than the chest. The adult sized bell is thus too large to be used on such a location. Since the diaphragm and bell are not removable, various attempts have been made to adapt the dual head stethoscope for multiple uses, i.e. for use with infants as well as adults. For example, U.S. Pat. No. 4,502,562 issued to Carl T. Nelson discloses and claims a stethoscope head with an insert which decreases the surface area of the bell, making it suitable for use with infants.

Another example of the adaptable stethoscope is commonly known as the "Sprague." The Sprague stethoscope is a stethoscope configuration which includes a chest piece including a drum and a stem, and removable diaphragm structures and bell components which attach to the drum. The diaphragm structure includes a disc, attachable to the drum; a ring, attachable to the disc; and a thin diaphragm attachable to the ring. The diaphragm structures and bell components are typically screwed on to the drum. The diaphragm structures and bell components are in various sizes so that the stethoscope may be adapted for use on infants or adults, or on areas where less skin area is available, such as between the ribs. The Sprague stethoscope is further equipped with a dual tube sound passage, which increases the area of the sound passage, thereby increasing the overall sound conductivity. The stem of the chest piece must include an adapter so that both tubes may be connected. FIGS. 4, 5, and 6 illustrate an embodiment of the Sprague stethoscope, including the elements of the diaphragm structure.

A desirable attribute of these stethoscopes is that they increase the usefulness of the particular stethoscope. The stethoscope head disclosed in the Nelson patent presents an insert for the bell portion of a typical dual head chest piece. However, the diaphragm is not adapted, and thus a second stethoscope is still necessary if the user wishes to use a diaphragm sided stethoscope on an infant. The Sprague stethoscope offers the user more useful adaptations of the dual head stethoscope, but because of the dual tubing and additional stem adapter, the stethoscope is heavier than the conventional stethoscope, and more costly to make.

Therefore, there is a need for a lightweight multiple use stethoscope that offers the usefulness of the Sprague stethoscope, but is not as cumbersome, or costly. The subject invention satisfies this need.

SUMMARY OF THE INVENTION

The present invention resides in a convertible stethoscope which offers the weight and cost advantages of a dual head stethoscope and the utility of a Sprague stethoscope. Briefly, and in general terms, the stethoscope of the invention includes a chest piece including a stem and a drum, and detachable diaphragm structures and bell components. The diaphragm structures and bell components, which attach to the drum of the chest piece, are of various sizes so that the same chest piece may be used with infants, adults, or on areas with less exposed skin, such as between the ribs, or around the clavicle. The stem of the chest piece is connected to a single tube, through which the sounds detected by the chest piece are transmitted. An ear piece is connected to the single tube at the end opposite the chest piece, for receiving transmitted sounds.

It will be appreciated from the foregoing that the present invention represents a significant advance in the field of stethoscopes. In particular, the invention provides a highly useful stethoscope, which may be used in a variety of circumstances. Moreover, as the stethoscope only uses a single tube as a sound passage, the stem of the chest piece does not require an additional, weighty adapter. The stethoscope is therefore not as big, heavy or cumbersome as the dual tube Sprague stethoscope, nor as costly to manufacture. Other aspects and advantages of the invention will become apparent from the following more detailed description, taken in conjunction with the accompanying drawings.

BRIEF DESCRIPTION OF THE DRAWINGS

FIG. 2 is a top view of a dual head chest piece with tube;

FIG. 3 is an elevated side view of the dual head chest piece;

FIG. 4 is a top view of a Sprague chest piece showing the dual tubing system;

FIG. 5 is an elevated side view of the Sprague chest piece, showing the adapter used to connect the dual tubing system;

DETAILED DESCRIPTION OF THE INVENTION

Figure 1:
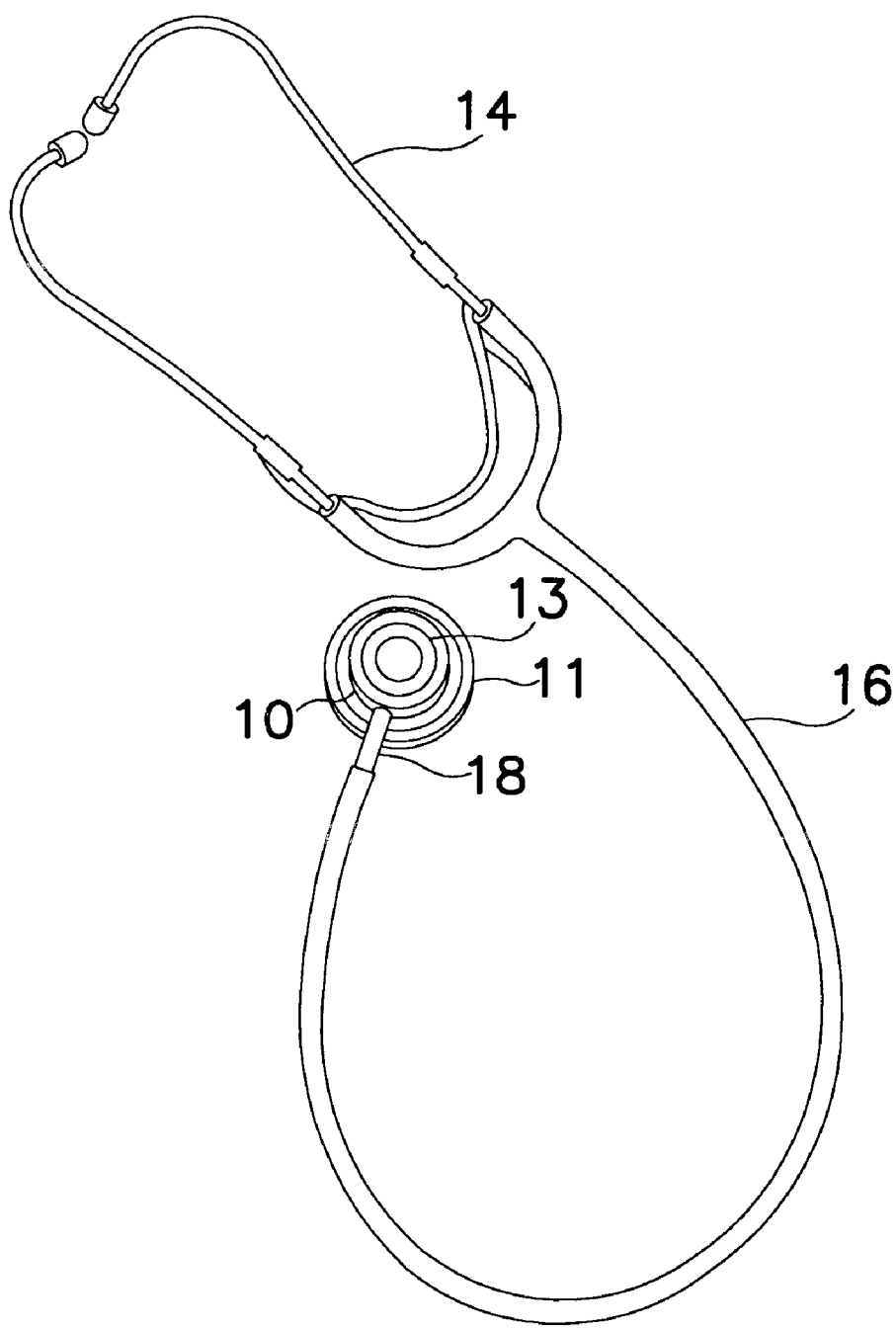
FIG. 1 is perspective view of a stethoscope in accordance with the present invention.
Figure 2:
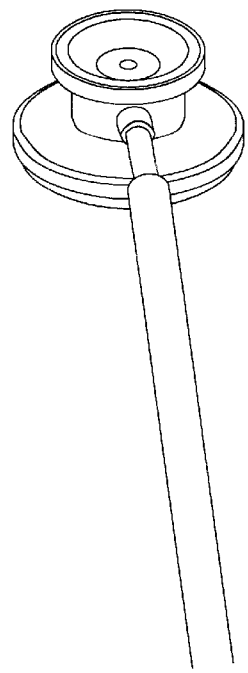
FIGS. 2–5 illustrate the prior art stethoscopes.
Figure 3:
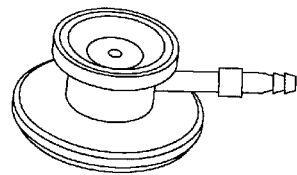
Figure 4:
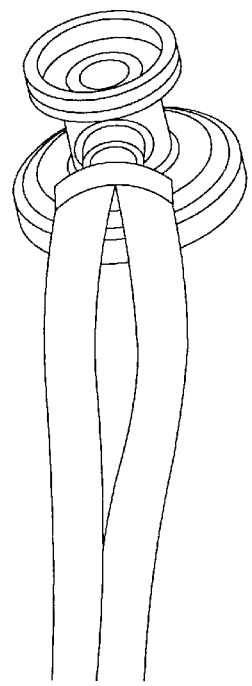
Figure 5:
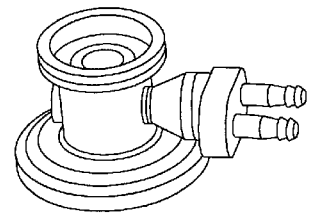
Figure 6:
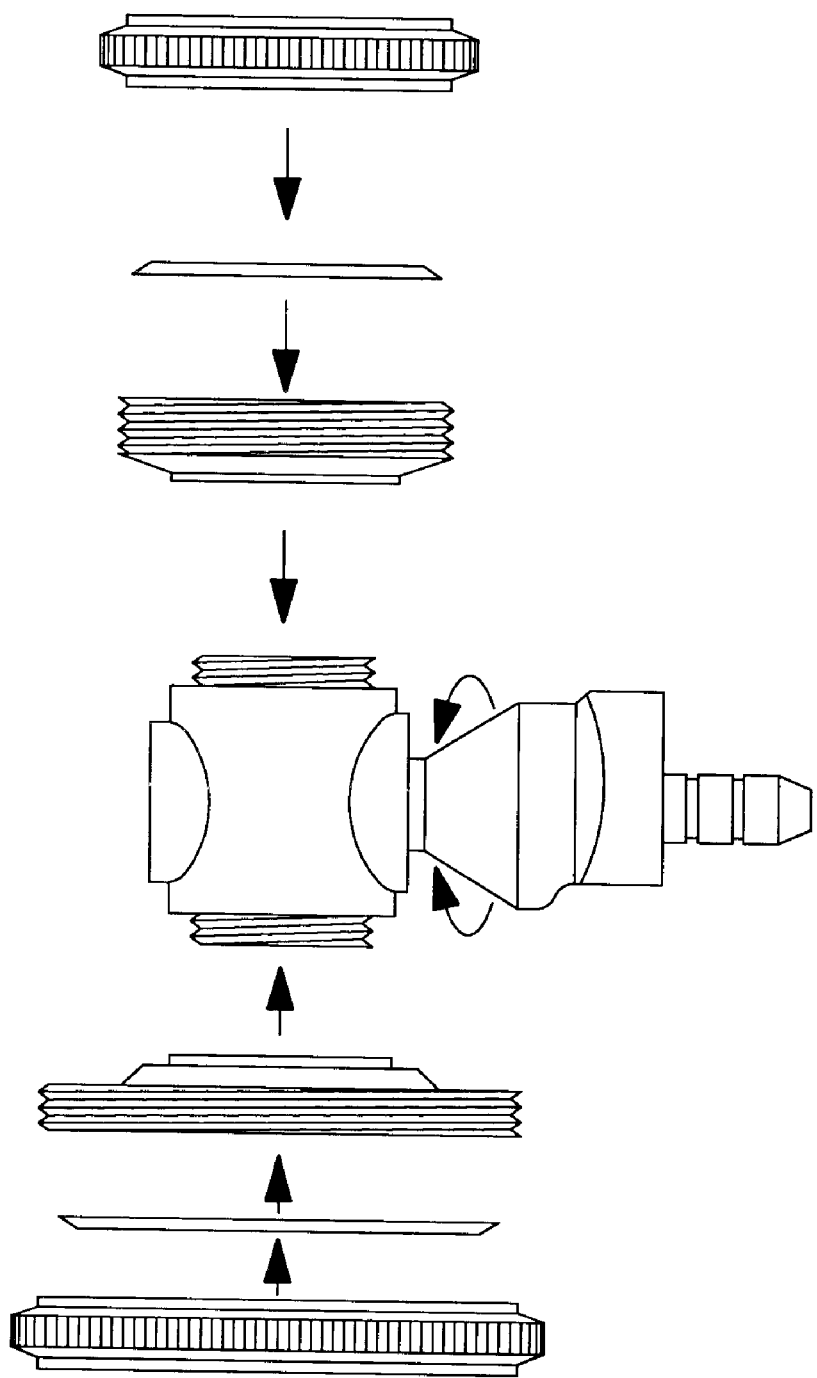
FIG. 6 is a side view of the principal components of the chest piece of the Sprague stethoscope, including the components of the large and small diaphragm structures.

As shown in the drawings for purposes of illustration, the present invention pertains to a stethoscope.

More specifically, FIG. 1 shows an embodiment of the subject invention. The invention includes a chest piece 10 having a drum 20 with removable large diaphragm structure 11 and removable small diaphragm structure 13, an ear piece, indicated by reference numeral 14, preferably a binaural type, a single sound tube 16 for conducting the sounds detected through chest piece 10 to ear piece 14. Sound tube 16 is connected to chest piece 10 at revolvable valve stem 18.

Figure 7:
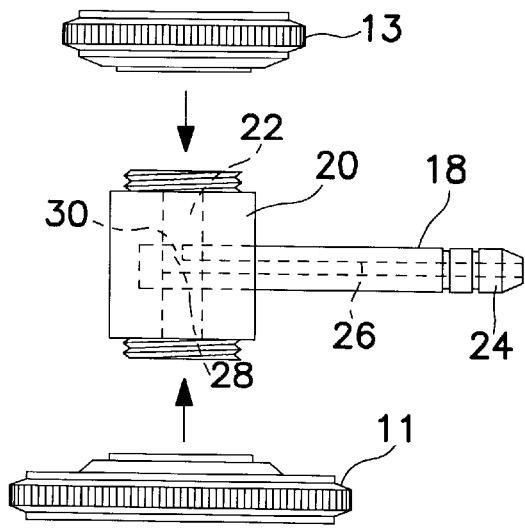
FIG. 7 is a side view of the principal components of the chest piece of the invention, shown with the large and small diaphragm structures.
Figure 8:
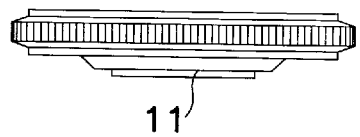
FIGS. 8–12 are side views of the various diaphragm structures and bell components of the chest piece.
Figure 9:
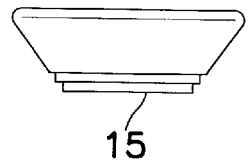
Figure 10:
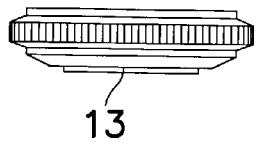
Figure 11:
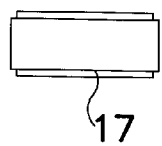
Figure 12:
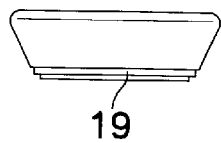

FIG. 7 shows the principal components of the chest piece of the invention. Drum 20 has a bore 22 running from one end to an opposite end. Large diaphragm structure 11 and small diaphragm structure 13 are attachable to each of the two ends of the drum. Valve stem 18 is partially inserted into drum 20, perpendicular to bore 22, so that a portion of the stem 24 protrudes. A concentric channel 26 runs within valve stem 18 perpendicular to bore 22, from the protruding end 24 to an intermediate point 28 within the valve stem. A perpendicular bore 30 runs from the end of the channel within the valve stem, through the wall of the valve stem. By revolving valve stem 18, perpendicular bore 26 may be aligned with bore 22 to form a sound passage, as also shown in FIG. 7. It will be appreciated that large diaphragm structure 11 and small diaphragm structure 13 can be replaced with other sized diaphragm structures or bell components, depending on the user's needs as shown below.

Figure 13:
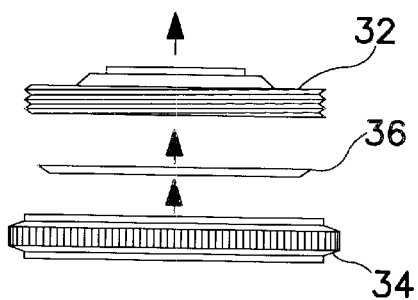
FIG. 13 is a side view of the principal components of a diaphragm structure.
Figure 14:
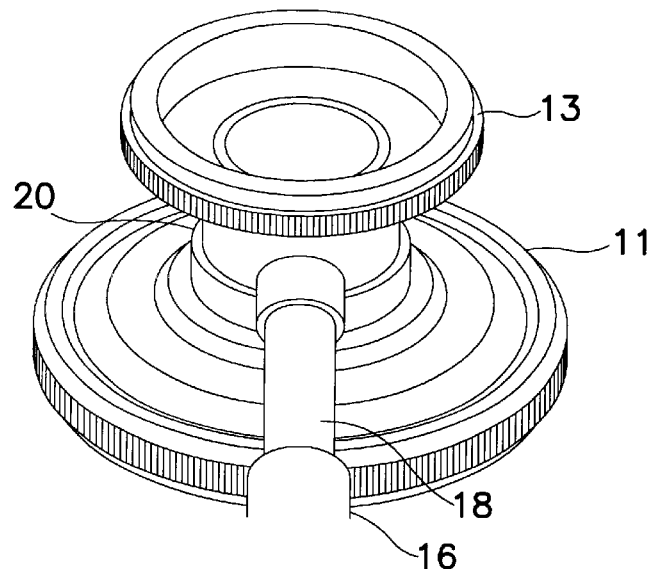
FIG. 14 is an elevated side view, showing the chest piece equipped with the large and small diaphragm structures.

As indicated in FIGS. 8–12, the diaphragm structures and bell components may include large diaphragm structure 11, small diaphragm structure 13, large bell component 15, or small bell component 17. As further illustrated in FIGS. 8–12, the bell components may include a mid-sized bell component 19, for use in narrow applications, such as auscultating a region near the ribs or clavicle of the patient. Each diaphragm structure or bell component may be fitted to either end of drum 20, thus allowing the user to select the desired sizes depending on the patient's diagnostic needs. As shown in FIG. 13, the diaphragm structure includes a disc 32, a ring 34 attachable to the disc, and a diaphragm 36 attachable to the ring. Disc 32 of the diaphragm structure is attachable to either end of drum 20. FIG. 14 shows an embodiment of chest piece 10 fitted with large diaphragm structure 11 and small diaphragm structure 13.

In a preferred embodiment of the invention, sound tube 16 is made of 40–44 gram tubing, preferably 42 gram tubing, which is thicker than tubing typically used with stethoscopes. The tubing provides better sound conductivity than the conventional tubing.

Figure 15:
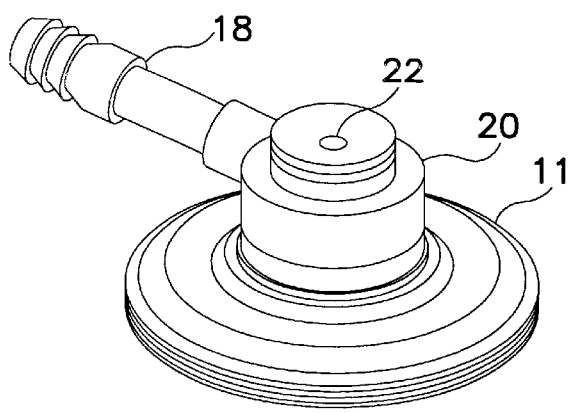
FIG. 15 is an elevated side view of the chest piece, illustrating the threading of the drum.

Although the diaphragm structures and bell components may be attached to drum 20 in many ways, such as the conventional snap lock manner as commonly used with milk bottle tops, it is preferred, as shown in FIGS. 7 and 15, that drum 20 have threads. Disc 32 of the diaphragm structures and the bell components have internal threads, so that the diaphragm structure or bell component is screwed to the drum. Thus, the diaphragm structure or bell component forms a tight seal with the drum, which reduces leaks that could interfere with the detection of sounds.

It will be appreciated from the foregoing that the subject invention represents a significant advance in the field of stethoscopes. In particular, the invention provides a stethoscope with all the versatility of the conventional Sprague stethoscope, that is smaller, less weighty and less cumbersome. The single tube sound passage, which is lighter and smaller than the dual tubing system, and does not require an adapter, reduces the manufacturing costs of the stethoscope, and thus also reduces the price for the stethoscope.

It will also be appreciated that, although a specific embodiment of the invention has been described in detail by way of example, various modifications may be made without departing from the spirit and scope of the invention, which should not be limited except as by the accompanying claims.

We claim:

1. A stethoscope including an ear piece for detecting sounds, comprising:

a chest piece including a body having ends, further having a bore therein, running from one end to another end, and detachable diaphragm structures and bell components, wherein the diaphragm structures and bell components include diaphragm structures and bell components of varying sizes so that the stethoscope may be used with infants, or with adults, connectable to each end of the chest piece;

a revolvable valve stem having ends, disposed partially within the chest piece, so that one end of the valve stem is within the chest piece and a single portion of the valve stem protrudes from the chest piece, the valve stem having means for transmitting sounds detected by the diaphragm structures and bell components from one end of the valve stem to the opposite end of the valve stem;

a single sound conducting tube having a range of 40 to 44 gram wall tubing connected at one end to the ear piece and at the other end to the portion of the revolvable valve stem which protrudes from said chest piece.

2. A stethoscope as defined in claim 1, wherein:

the single sound conducting tube is 42 gram walled tubing.

3. A stethoscope as defined in claim 1, wherein:

each end of the chest piece is threaded; and, the detachable diaphragm structures and bell components further comprise threading so that the structures and components are connected by meshing the threading of the components with the threading of the chest piece.

4. A stethoscope as defined in claim 1, wherein:

the revolvable valve stem is disposed perpendicular to the bore of the chest piece body, the revolvable valve stem having a channel, and an inner and outer surface, the channel running from a protruding end of the valve stem to a point within the stem, the valve stem further has a bore perpendicular to the channel, running from the channel to the outer surface of the valve stem, so that when the valve stem is rotated within the chest piece, the bore of the valve stem aligns with the bore of the chest piece, forming a sound passage through the channel of the valve stem.

* * * * *